United States Patent
Tsuyuki

(10) Patent No.: US 10,758,203 B2
(45) Date of Patent: Sep. 1, 2020

(54) X-RAY COMPUTED TOMOGRAPHY APPARATUS

(71) Applicant: Canon Medical Systems Corporation, Otawara-shi (JP)

(72) Inventor: Masaharu Tsuyuki, Nasushiobara (JP)

(73) Assignee: Canon Medical Systems Corporation, Otawara-shi (JP)

( * ) Notice: Subject to any disclaimer, the term of this patent is extended or adjusted under 35 U.S.C. 154(b) by 107 days.

(21) Appl. No.: 16/058,492

(22) Filed: Aug. 8, 2018

(65) Prior Publication Data
US 2019/0046151 A1    Feb. 14, 2019

(30) Foreign Application Priority Data

Aug. 8, 2017  (JP) .................................. 2017-153435
Aug. 6, 2018  (JP) .................................. 2018-147877

(51) Int. Cl.
| | | |
|---|---|---|
| A61B 6/03 | (2006.01) | |
| A61B 6/00 | (2006.01) | |
| G01T 1/17 | (2006.01) | |
| G01T 1/29 | (2006.01) | |

(52) U.S. Cl.
CPC .............. *A61B 6/585* (2013.01); *A61B 6/032* (2013.01); *A61B 6/405* (2013.01); *G01T 1/17* (2013.01); *G01T 1/2985* (2013.01); *A61B 6/545* (2013.01); *A61B 6/583* (2013.01)

(58) Field of Classification Search
None
See application file for complete search history.

(56) References Cited

U.S. PATENT DOCUMENTS

| | | | | |
|---|---|---|---|---|
| 5,430,785 | A * | 7/1995 | Pfoh ...................... | A61B 6/032 378/19 |
| 10,206,650 | B2 * | 2/2019 | Rozas .................... | A61B 6/032 |
| 10,398,405 | B2 * | 9/2019 | Rozas .................... | H01J 35/106 |
| 2013/0020478 | A1 | 1/2013 | Takasaki | |
| 2016/0015357 | A1 * | 1/2016 | Rozas .................... | A61B 6/032 378/207 |
| 2019/0046151 | A1 * | 2/2019 | Tsuyuki ................. | A61B 6/405 |
| 2019/0192106 | A1 * | 6/2019 | Rozas .................... | A61B 6/032 |

FOREIGN PATENT DOCUMENTS

| | | |
|---|---|---|
| JP | 2007-125129 | 5/2007 |
| JP | 2013-24784 | 2/2013 |

* cited by examiner

*Primary Examiner* — Thomas R Artman
(74) *Attorney, Agent, or Firm* — Oblon, McClelland, Maier & Neustadt, L.L.P.

(57) ABSTRACT

According to one embodiment, an X-ray computed tomography apparatus includes an X-ray tube, an X-ray detector, a gantry, control circuitry, and acquisition circuitry. The X-ray tube generates X-rays. The X-ray detector detects the X-rays generated by the X-ray tube. The gantry supports the X-ray tube and the X-ray detector rotatably around a rotation axis. While the X-ray tube and the X-ray detector are rotated, the control circuitry allows the X-ray tube to generate X-rays and alters a predetermined CT imaging parameter for which correction data is acquired during a single rotation. While the X-ray tube and the X-ray detector are rotated, the acquisition circuitry acquires correction data related to the target CT imaging parameter through the X-ray detector.

9 Claims, 13 Drawing Sheets

| CT imaging parameter | Setting values |
|---|---|
| Focus size | Small, Medium, Large |
| Focus position | −1cm〜+1cm |
| Tube voltage | 50kV〜150kV |
| Tube current | 50mA〜1000mA |
| DAS gain | 1〜100 |
| Slit opening width | 1mm〜100mm |
| DAS bundle unit | 0.5mm,1.0mm,2.0mm,4.0mm,8.0mm |
| ⋮ | ⋮ |

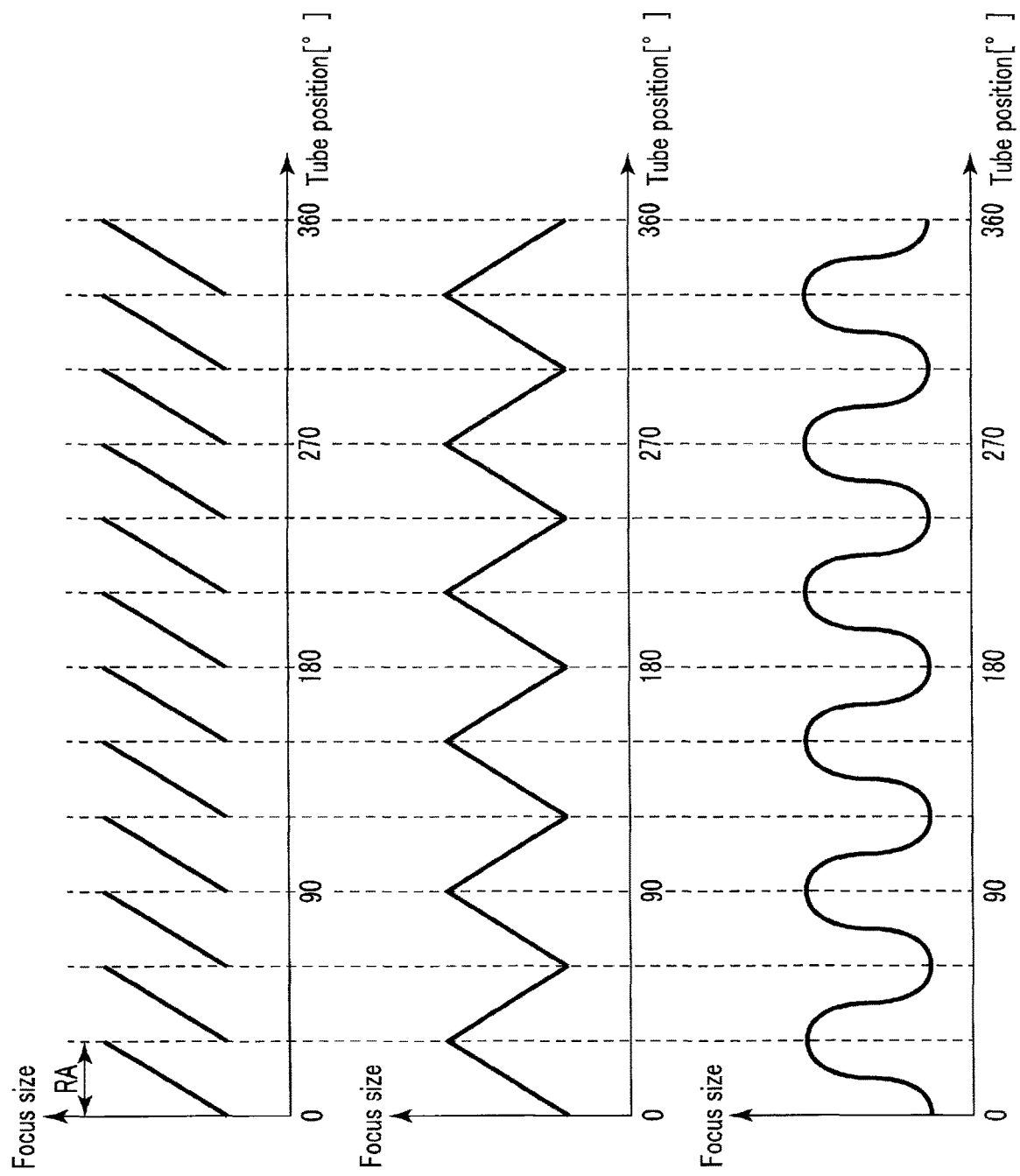
F I G. 8

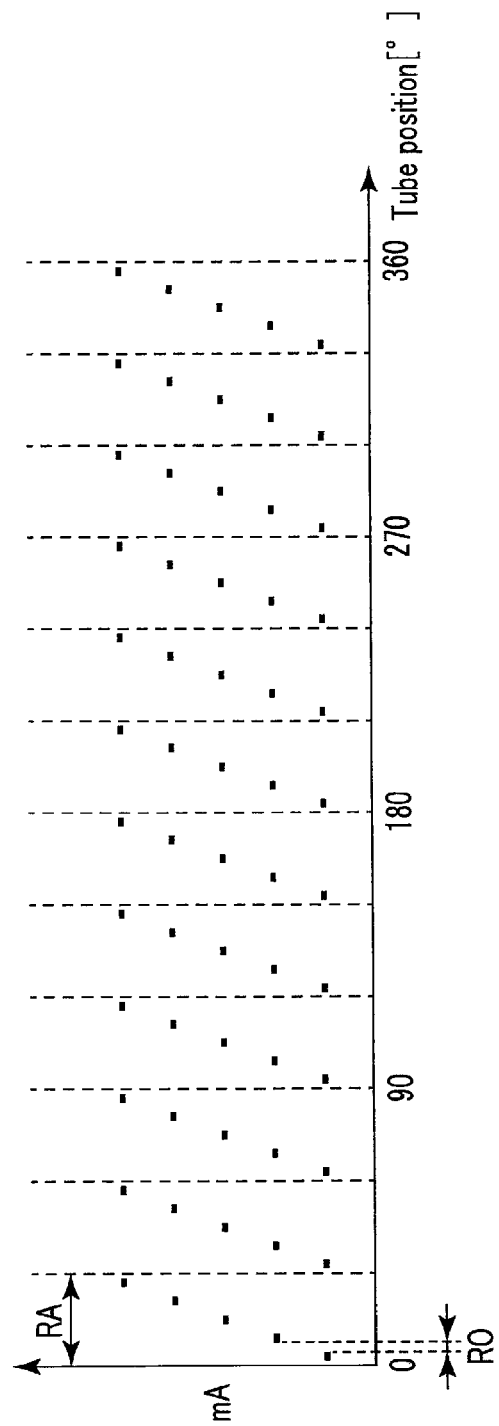
F I G. 12

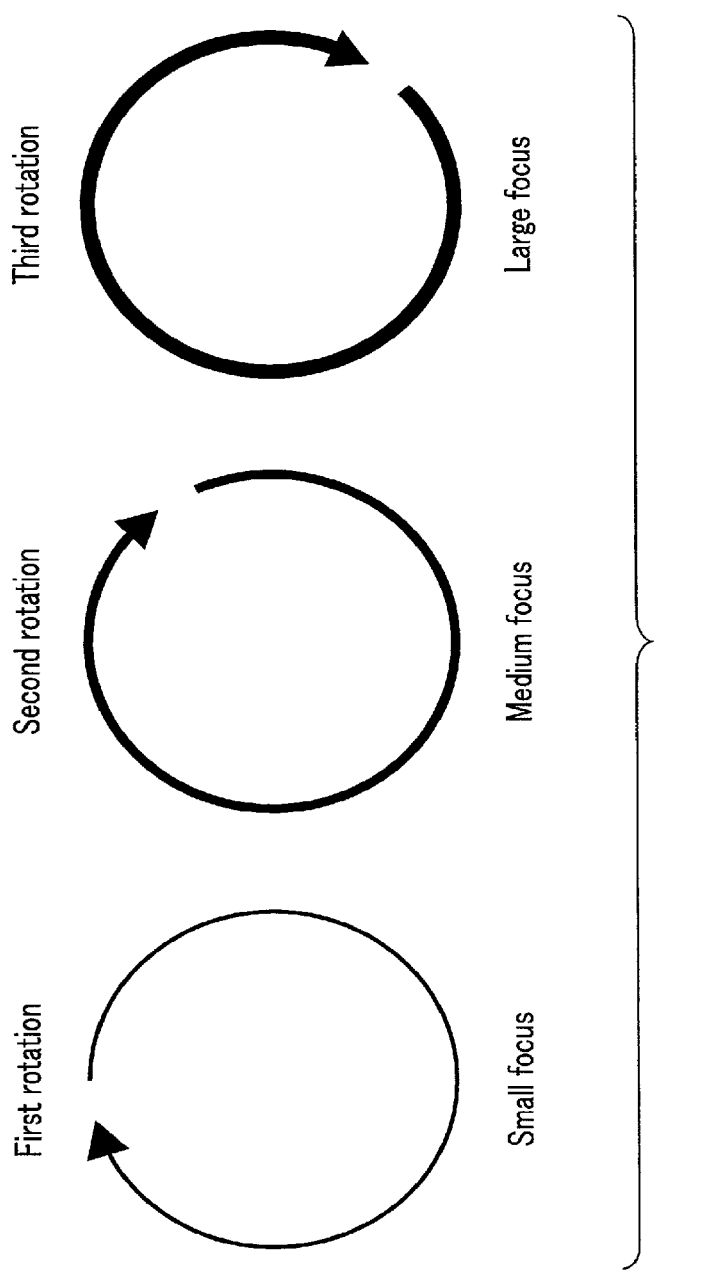

X-RAY COMPUTED TOMOGRAPHY APPARATUS

CROSS-REFERENCE TO RELATED APPLICATIONS

This application is based upon and claims the benefit of priority from the Japanese Patent Application No. 2017-153435, filed Aug. 8, 2017, and the Japanese Patent Application No. 2018-147877, filed Aug. 6, 2018 the entire contents of all of which are incorporated herein by reference.

FIELD

Embodiments described herein relate generally to an X-ray computed tomography apparatus.

BACKGROUND

X-ray computed tomography apparatuses provided with a high-voltage X-ray device capable of altering CT imaging parameters such as a tube voltage are already known. For such X-ray computed tomography apparatuses, it is necessary to acquire correction data for calibration, etc., for respective tube voltage values. The correction data for a tube voltage value is acquired during a rotation of an X-ray tube and an X-ray detector. Accordingly, the time required for acquiring correction data increases as the number of types or levels of variable CT imaging parameters increases.

BRIEF DESCRIPTION OF THE DRAWINGS

FIG. 8 illustrates a CT imaging parameter acquisition sequence related to a correction data acquisition scan according to Example 2.
FIG. 12 illustrates a correction data acquisition sequence according to Example 5.

FIG. 14 illustrates a concept of a standard method for acquiring correction data.

DETAILED DESCRIPTION

In general, according to one embodiment, an X-ray computed tomography apparatus includes an X-ray tube, an X-ray detector, a gantry, control circuitry, and acquisition circuitry. The X-ray tube generates X-rays. The X-ray detector detects the X-rays generated by the X-ray tube. The gantry supports the X-ray tube and the X-ray detector rotatably around a rotation axis. While the X-ray tube and the X-ray detector are rotated, the control circuitry allows the X-ray tube to generate X-rays and alters a predetermined CT imaging parameter for which correction data is acquired during a single rotation. While the X-ray tube and the X-ray detector are rotated, the acquisition circuitry acquires correction data related to the predetermined CT imaging parameter through the X-ray detector.

In the following, the X-ray computed tomography apparatus according to the present embodiment will be explained with reference to the drawings.

Figure 1:
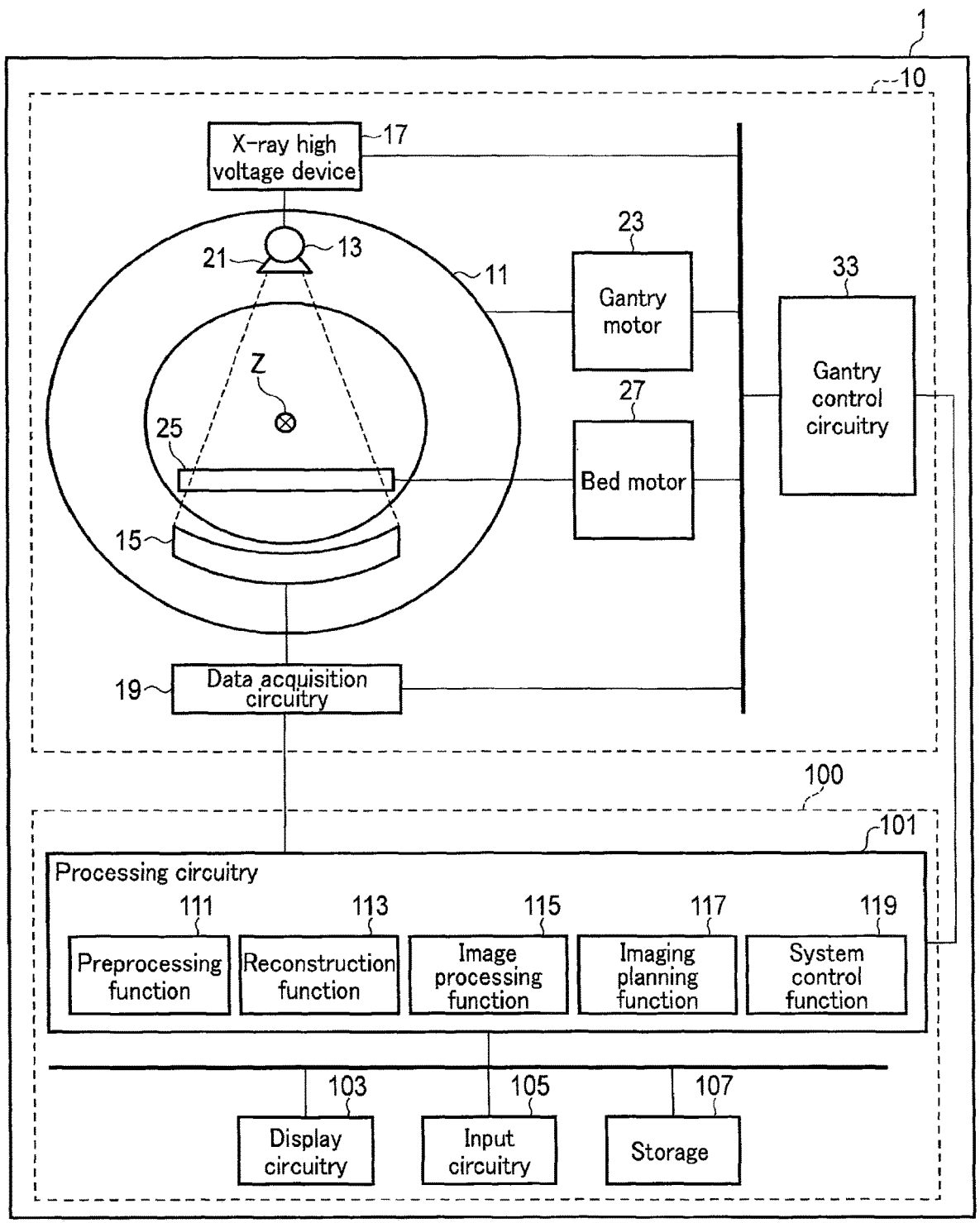
FIG. 1 illustrates the configuration of the X-ray computed tomography apparatus according to the present embodiment.

FIG. 1 illustrates the configuration of an X-ray computed tomography apparatus 1 according to the present embodiment. As shown in FIG. 1, the X-ray computed tomography apparatus 1 according to the present embodiment includes a gantry 10, and a console 100. For example, the gantry 10 is installed in a CT examination room, and the console 100 is installed in a control room adjacent to the CT examination room. The gantry 10 and the console 100 are communicably connected to each other. The gantry 10 includes an imaging mechanism configured to perform X-ray CT imaging. The console 100 is a computer that controls the gantry 10.

As shown in FIG. 1, the gantry 10 includes a rotation frame 11 of an essentially cylindrical shape, which includes a bore. The rotation frame 11 is also referred to as a "rotation unit." As shown in FIG. 1, an X-ray tube 13 and an X-ray detector 15, arranged to face each other via the bore, are attached to the rotation frame 11. The rotation frame 11 is a metal frame made, for example, of aluminum, in an annular shape. The gantry 10 includes a main frame made of metal, such as aluminum. The main frame is also referred to as a "stationary unit." The rotation frame 11 is rotatably supported by the main frame.

The X-ray tube 13 generates X-rays. The X-ray tube 13 includes a vacuum tube with a cathode that generates thermoelectrons, an anode that generates X-rays by receiving the thermoelectrons traveled from the cathode, and grid electrodes provided between the cathode and the anode. The X-ray tube 13 is connected to a high-voltage X-ray device 17 via a high voltage cable. The high-voltage X-ray device 17 applies a tube voltage between the cathode and the anode. Thermoelectrons travel from the cathode to the anode upon application of the tube voltage. A tube current flows via thermoelectrons traveling from the cathode to the anode tube. A part of the anode with which thermoelectrons collide is referred to as a "focus." The high-voltage X-ray device 17 applies a bias voltage between the grid electrodes. The thermoelectrons traveling from the cathode to the anode are deflected due to application of the bias voltage. Namely, a tube current, the focus size and a focus position may be altered via adjustment of the bias voltage.

The high-voltage X-ray device 17 may adopt any type of high voltage generator such as a transformer type X-ray high voltage generator, a constant voltage type X-ray high voltage generator, a capacitor type X-ray high voltage generator, or an inverter type X-ray high voltage generator. The high-voltage X-ray device 17 is attached, for example, to the rotation frame 11. The high-voltage X-ray device 17 adjusts an X-ray parameter such as a tube voltage, a tube current; the X-ray focus size, the X-ray focus position, etc. in accordance with the control by a gantry control circuitry 33.

The X-ray tube 13 is provided with a collimator 21. The collimator 21 aligns the X-rays generated by the X-ray tube 13. Specifically, the collimator 21 includes an X-ray shielding plate that possesses a variable slit opening. The collimator 21 adjusts the width of the slit opening by moving the X-ray shielding plate upon receiving power from a gantry motor 23.

As shown in FIG. 1, the rotation frame 11 rotates about a rotation axis Z at a predetermined angular velocity upon receiving power from the gantry motor 23. The rotation frame 11 receives power from the gantry motor 23 to title around an axis of tilt horizontally orthogonal to the rotation axis Z. The gantry motor 23 is housed, for example, in the gantry 10.

The gantry motor 23 generates power to drive the collimator 21 to adjust the slit opening width upon receiving a driving signal from the gantry control circuitry 33. The gantry motor 23 also generates power to rotate or tilt the rotation frame 11 upon receiving a driving signal from the gantry control circuitry 33. The gantry motor 23 may be any motor such as a direct drive motor, a servo motor, etc.

An FOV is set in the bore of the rotation frame 11. A top plate supported by a bed 25 is inserted into the bore of the rotation frame 11. A subject is placed on the top plate. The bed 25 movably supports the top plate. A bed motor 27 is housed in the bed 25. The bed motor 27 generates power to move the top plate in the longitudinal direction, the vertical direction, and the widthwise direction upon receiving a driving signal from the gantry control circuitry 33. The bed 25 regulates the top plate so that an imaging target portion of the subject is included within the FOV.

The X-ray detector 15 detects X-rays generated by the X-ray tube 13. Specifically, the X-ray detector 15 includes a plurality of detection elements arranged on a two-dimensional curved surface. The X-ray detection elements each include a scintillator and an optical sensor. The scintillator is formed of a material that converts X-rays into photons. The scintillator converts the applied X-rays into light having the photon amount corresponding to the intensity of the applied X-rays. The optical sensor is a circuit element that amplifies light generated from the scintillator and converts the light into an electric signal. For example, a photomultiplier tube or a photodiode, etc. is applied as the optical sensor. The detection elements may adopt an indirect conversion type detection element that converts X-rays into photons and then detects the photons, or a direct conversion type detection element that directly converts X-rays into an electric signal.

Data acquisition circuitry 19 is connected to the X-ray detector 15. The data acquisition circuitry 19 reads from the X-ray detector 15 an electric signal in accordance with the dose of X-rays detected by the X-ray detector 15, amplifies the read electric signal with a variable amplification rate (hereinafter referred to as "DAS gain"), integrates the electric signal over a view period to acquire raw data with a digital value in accordance with the dose of X-rays over the view period. The DAS gain is adjusted by the gantry control circuitry 33. The data acquisition circuitry 19 is implemented by, for example, an ASIC (Application Specific Integrated Circuit) on which a circuit element capable of generating raw data is mounted. In the present embodiment, raw data acquired for calibration is referred to as "correction data." The data acquisition circuitry 19 includes a switch that alters bundle units of read channels of the detection elements. The bundle units are referred to as DAS bundle units. The switch is provided as a preprocessing stage of integration circuitry that generates an integration signal, or at a preprocessing stage of an A/D converter that converts an integration signal to raw data. The data acquisition circuitry 19 controls the switch in response to an instruction from the gantry control circuitry 33 to alter the DAS bundle units.

As shown in FIG. 1, the gantry control circuitry 33 synchronously controls the high-voltage X-ray device 17, the data acquisition circuitry 19, the gantry motor 23, and the bed motor 27, to perform X-ray CT imaging in accordance with imaging conditions obtained from the processing circuitry 101 of the console 100. The gantry control circuitry 33 according to the present embodiment performs X-ray CT imaging for acquiring correction data (hereinafter referred to as "correction data acquisition scan"). The gantry control circuitry 33 includes a processor, such as a CPU (Central Processing Unit) and an MPU (Micro Processing Unit), etc. and a memory, such as a ROM (Read Only Memory) and a RAM (Random Access Memory), etc. as hardware resources. The gantry control circuitry 33 may be implemented by an ASIC or an FPGA (Field Programmable Gate Array), a CPLD (Complex Programmable Logic Device), or an SPLD (Simple Programmable Logic Device).

As shown in FIG. 1, the console 100 includes the processing circuitry 101, display circuitry 103, input circuitry 105, and a storage 107. Data communication is performed between the processing circuitry 101, the display circuitry 103, the input circuitry 105, and the storage 107 via a bus.

The processing circuitry 101 includes a processor such as a CPU, an MPU, or a GPU (Graphics Processing Unit), etc. and a memory such as a ROM or a RAM, etc. as hardware resources. The processing circuitry 101 executes various types of programs to implement a preprocessing function 111, a reconstruction function 113, an image processing function 115, an imaging planning function 117, and a system control function 119. The preprocessing function 111, the reconstruction function 113, the image processing function 115, the imaging planning function 117, and the system control function 119 may be implemented either by the processing circuitry 101 on a single substrate, or by the processing circuitry 101 on a plurality of substrates.

Via the preprocessing function 111, the processing circuitry 101 performs preprocessing, such as logarithmic conversion to raw data transmitted from the gantry 10. The preprocessed raw data is also referred to as "projection data." The processing circuitry 101 performs calibration based on the correction data transmitted from the gantry 10.

Via the reconstruction function 113, the processing circuitry 101 generates a CT image representing a space distribution of CT values related to the subject, based on the preprocessed raw data. The known image reconstruction algorithm such as an FBP (Filtered Back Projection) method or a successive approximation reconstruction method, may be adopted.

Via the image processing function 115, the processing circuitry 101 performs various types of image processing to a CT image reconstructed by the reconstruction function 113. For example, the processing circuitry 101 performs three-dimensional image processing, such as volume rendering, surface volume rendering, pixel value projection processing, MPR (Multi-Planer Reconstruction) processing, and CPR (Curved MPR) processing, etc. to the CT image to generate a display image.

Via the imaging planning function 117, the processing circuitry 101 generates an imaging plan for the correction data acquisition scan automatically or in accordance with a user's instruction through the input circuitry 105.

Via the system control function 119, the processing circuitry 101 integrally controls the X-ray computed tomography apparatus 1 according to the present embodiment. Specifically, the processing circuitry 101 reads a control program stored in the storage 107, deploys the control program on a memory, and controls the respective units of the X-ray computed tomography apparatus 1 in accordance with the deployed control program.

The display circuitry 103 displays various types of data such as a plan of correction data acquisition scan, a CT image, etc. For example, a CRT display, a liquid crystal display, an organic EL display, an LED display, a plasma display, or any other displays known in this technical field can be discretionarily applied as the display circuitry 103.

The input circuitry 105 inputs various types of instructions from the user. Specifically, the input circuitry 105 includes an input device and an input interface. The input device receives various types of instructions from the user. A keyboard, a mouse, a trackball, a joystick, or switches etc. may be used as the input device. The input interface supplies an output signal from the input device to the processing circuitry 101 via a bus.

The storage 107 is a storage unit, such as an HDD, an SSD, or an integrated circuit storage unit, configured to store various types of information. The storage 107 may also be a drive, etc. which reads and writes various types of information to and from portable storage media, such as a CD-ROM drive, a DVD drive, and a flash memory. For example, the storage 107 stores a control program, etc. for the correction data acquisition scan, etc. according to the present embodiment.

In the following description, the operation of the X-ray computed tomography apparatus 1 according to the present embodiment will be explained in detail.

The gantry control circuitry 33 according to the present embodiment performs a correction data acquisition scan to acquire correction data, as described above. During the correction data acquisition scan, correction data is acquired by performing a CT scan on a phantom which mainly consists of a basic substance such as air (i.e., no phantom or subject) or water, etc. The correction data is used for calibration of a CT value conversion factor, or calibration of a positional shift of the X-ray tube 13 or the X-ray detector 15, etc. The correction data is acquired for each possible value of a CT imaging parameter. The CT imaging parameter according to the present embodiment may be a focus size, a focus position, a tube voltage, a tube current, a DAS gain, a slit opening width, DAS bundle units, etc. The output of the sensitivity of the X-ray detector 15 is dependent from an angle about the rotation axis Z (hereinafter referred to as a "rotation angle"). Accordingly, it is necessary to acquire correction data at different rotation angles for each type and each possible value of the CT imaging parameter. Thus, the correction data need to be effectively acquired.

FIG. 14 illustrates a concept of a standard method for acquiring correction data. In FIG. 14, the CT imaging parameter is assumed to be a focus size. As shown in FIG. 14, it is assumed that correction data for a focus of a small size (small focus), correction data for a focus of a medium size (medium focus), and correction data for a focus of a large size (large focus) are acquired. In the standard method, the focus size is first set to a small focus, and correction data is acquired during a first rotation of the X-ray tube 13 and the X-ray detector 15; the focus size is altered to a medium focus, and correction data is acquired during a second rotation of the X-ray tube 13 and the X-ray detector 15; and then the focus size is altered to a large focus, and correction data is acquired during a third rotation of the X-ray tube 13 and the X-ray detector 15. It is necessary to rotate the X-ray tube 13 and the X-ray detector 15 for each focus size, and accordingly, the X-ray tube 13 and the X-ray detector 15 need to be rotated equal number of times to the number of levels of the focus size. Accordingly, the time required for acquisition of correction data and the number of processing steps increase as the number of types or levels of target CT imaging parameters increases.

Figures 2, 3:
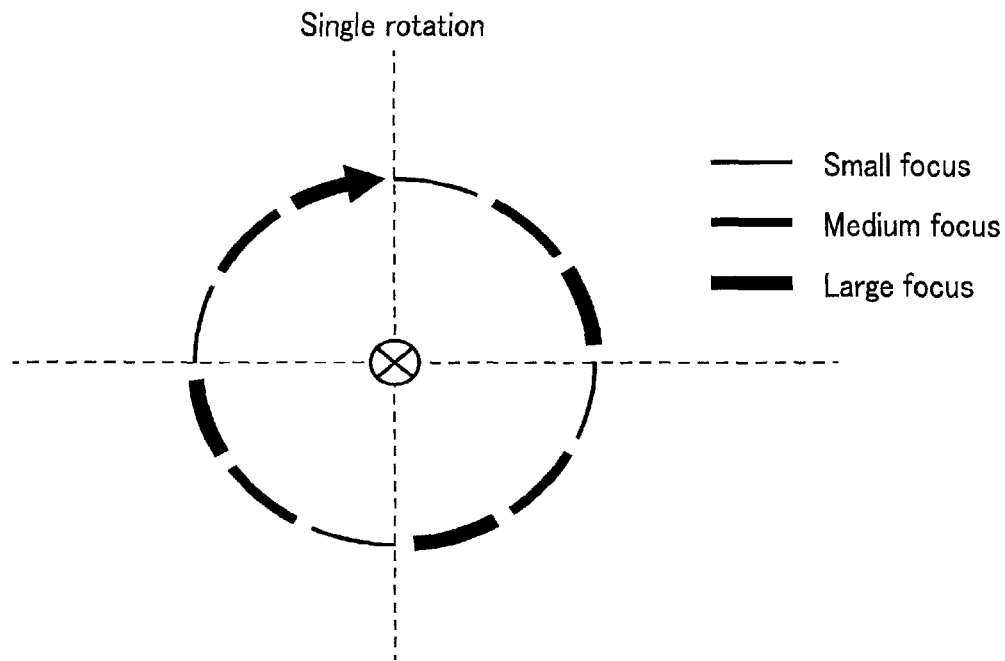
FIG. 2 illustrates a concept of a correction data acquisition scan according to the present embodiment.
FIG. 3 illustrates an example of a parameter table utilized by processing circuitry when activating an imaging planning function of FIG. 1.

FIG. 2 illustrates a concept of the correction data acquisition scan according to the present embodiment. In FIG. 2, the target CT imaging parameter is assumed to be a focus size, for comparison with FIG. 14. As shown in FIG. 2, during the correction data acquisition scan according to the present embodiment, correction data is acquired while the focus size is sequentially altered from a small focus, to a medium focus, and to a large focus in each predetermined unit angle range. Since the focus size is altered among the small focus, the medium focus, and the large focus in the predetermined unit angle range, correction data for the small focus, the medium focus, and the large focus can be acquired within a single rotation of the X-ray tube 13 and the X-ray detector 15. The predetermined unit angle range is an angle range which permits the change in output or sensitivity of the X-ray detector 15 relative to the rotation angle, i.e., an angle range in which the rotation angle dependency of the output or the sensitivity of the X-ray detector 15 can be ignored. In the following description, the predetermined angle range is referred to as a unit-allowable angle range.

While the X-ray tube 13 and the X-ray detector 15 are rotated (i.e., while the rotation frame 11 is rotated), the gantry control circuitry 33 according to the present embodiment controls the high-voltage X-ray device 17 to allow the X-ray tube 13 to generate X-rays, and controls at least one of the high-voltage X-ray device 17 or the data acquisition circuitry 19 to alter a predetermined CT imaging parameter with respect to the correction data to be acquired within a single rotation of the X-ray tube 13 and the X-ray detector 15. Specifically, while the X-ray tube 13 and the X-ray detector 15 are rotated (i.e., while the rotation frame 11 is rotated), the gantry control circuitry 33, according to the present embodiment, controls the high-voltage X-ray device 17 to allow the X-ray tube 13 to generate X-rays, and controls at least one of the high-voltage X-ray device 17 or the data acquisition circuitry 19 to alter a predetermined CT imaging parameter, with respect to which correction data is to be acquired within a predetermined parameter value range in each unit-allowable angle range.

First, the acquisition sequence construction for a CT imaging parameter according to the present embodiment will be described. The acquisition sequence of a CT imaging parameter is determined by the processing circuitry 101 by activating the imaging planning function 117. The imaging planning function 117 is executed when planning the correction data acquisition scan. By the imaging planning function 117, the processing circuitry 101 first uses a parameter table and determines an acquisition condition for the correction data acquisition scan. The parameter table is implemented by an LUT (Look Up Table) or a database.

FIG. 3 illustrates an example of a parameter table. As shown in FIG. 3, each of the CT imaging parameters is associated with setting values in the parameter table. For example, the CT imaging parameters registered in the parameter table include a focus size, a focus position, a tube voltage, a tube current, a DAS gain, a slit opening width, DAS bundle units, etc. The setting values are possible values of the respective CT imaging parameters with respect to the correction data to be acquired. For example, if the CT imaging parameter is the focus size, discrete values of a small focus, a medium focus, and a large focus are associated as the setting values with the focus size. If the CT imaging parameter is the focus position, the consecutive values from −1 cm to +1 cm are associated in the form of the setting values with the focus position. In each unit-allowable angle range, the parameter value of the CT imaging parameter is altered over the parameter value range from the lower limit value to the upper limit value of the setting values. The setting values shown in FIG. 3 are only examples, and are not limited thereto. For example, the setting values of the focus size may be four or more sizes, instead of three sizes of small focus, medium focus and large focus, or may be consecutive values from the lower limit size to the upper limit size. If the CT imaging parameter is DAS bundle units, the discrete values of 0.5 mm, 1.0 mm, 2.0 mm, 4.0 mm, and 8.0 mm are associated as the setting values with the DAS bundle units. The form of bundle is assumed to be a square. Accordingly, the setting value of "0.5 mm" indicates "length×width=0.5 mm×0.5 mm", for example. The form of bundle may be a rectangle.

Specifically, the processing circuitry 101 discretionarily selects a CT imaging parameter with respect to which correction data is to be acquired among the plurality of CT imaging parameters registered in the parameter table, automatically or manually in response to a user's instruction through the input circuitry 105. If a CT imaging parameter with respect to the correction data to be acquired is selected, the processing circuitry 101 specifies a setting value associated with the selected CT imaging parameter from the parameter table. The number of CT imaging parameter types with respect to the correction data to be acquired is not limited to one, but may be two or more. The setting values may be discretionarily modified from the values registered in the parameter table through the input circuitry 105, etc.

Via the imaging planning function 117, the processing circuitry 101 discretionarily sets the unit-allowable angle range from among predetermined multiple values. The processing circuitry 101 may set the unit-allowable angle range depending on the type of the CT imaging parameter with respect to the correction data to be acquired. For example, a unit-allowable angle range is determined in accordance with an angle range required to alter all the setting values of the corresponding CT imaging parameter, for example. If the CT imaging parameter is the focus size, and the setting values include a small focus, a medium focus, and a large focus, the unit-allowable angle range is set to be equal to or greater than an angle range required for altering the focus size to all of the small focus, the medium focus, and the large focus. In this case, the processing circuitry 101 includes a table or a database in which the types of CT imaging parameters are associated with the respective unit-allowable angle ranges. The processing circuitry 101 uses the table or the database, and automatically determines the unit-allowable angle range based on the CT imaging parameter with respect to the correction data to be acquired.

The processing circuitry 101 may determine, by activating the imaging planning function 117, the unit-allowable angle range in accordance with an acquisition condition for the correction data acquisition scan. The acquisition condition used for determination of the unit-allowable angle range may be, for example, a CT imaging parameter, a slice thickness, and a rotation speed of the rotation frame 11. For example, if the rotation speed is high, the centrifugal force affected upon the X-ray tube 13 or the X-ray detector 15 becomes large, which is likely to cause instability. Accordingly, the unit-allowable angle range is set to be relatively a small value. If the rotation speed is low, the centrifugal force affected upon the X-ray tube 13 or the X-ray detector 15 becomes small, which is unlikely to cause instability. Accordingly, the unit-allowable angle range is set to be relatively a large value. If the CT imaging parameter is the focus size, and the setting value is a large focus, the unit-allowable angle range is set to be a relatively large value, and if the setting value is a small focus, the unit-allowable angle range is set to be relatively a small value.

If the type of the CT imaging parameter, the setting value of the CT imaging parameter, and the unit-allowable angle range are determined, the processing circuitry 101 constructs an acquisition sequence of the CT imaging parameter based on the type and the setting value of the CT imaging parameter, and the unit-allowable angle range. The correction data acquisition scan does not need to take the imaging quality into account since no subject is imaged. Accordingly, even if the number of levels of the setting values of the CT imaging parameter to be altered during a rotation of the rotation frame 11 is greater than the number of levels of the parameter values used in a normal scan which requires the imaging quality to be accounted, the processing circuitry 101 constructs an acquisition sequence to alter the setting value to all levels in each unit-allowable angle range. Specifically, since the image quality is significantly degraded if the focus size is sequentially altered from the small focus, to the medium focus, and to the large focus during a rotation of the rotation frame 11, there is no advantage to sequentially alter the focus sizes during a rotation of the rotation frame 11 in the normal scan. On the other hand, the image quality is not important for the correction data acquisition scan, and accordingly, the limitation of the number of levels to maintain the image quality can be ignored. Namely, during the correction data acquisition scan according to the present embodiment, the focus size can be altered among the small focus, the medium focus, and the large focus within each unit-allowable angle range, and correction data for all the focus sizes: the small focus, the medium focus, and the large focus, can be acquired swiftly. In other words, the processing circuitry 101 can construct an acquisition sequence in which the parameter values of the CT imaging parameter can be altered in terms of the levels, the manner of change, and the degrees of change that are not acceptable for the normal scan which need to ensure the image quality, by focusing on the efficiency of correction data acquisition. Information on the constructed acquisition sequence (hereinafter referred to as "acquisition sequence information") is stored in the storage 107.

In the following description, various examples of the correction data acquisition scan will be explained.

EXAMPLE 1

The gantry control circuitry 33 according to Example 1 allows the X-ray tube 13 to generate X-rays, and discretely alters a CT imaging parameter for which correction data is acquired in each unit-allowable angle range during a rotation of the rotation frame 11.

Figure 4:
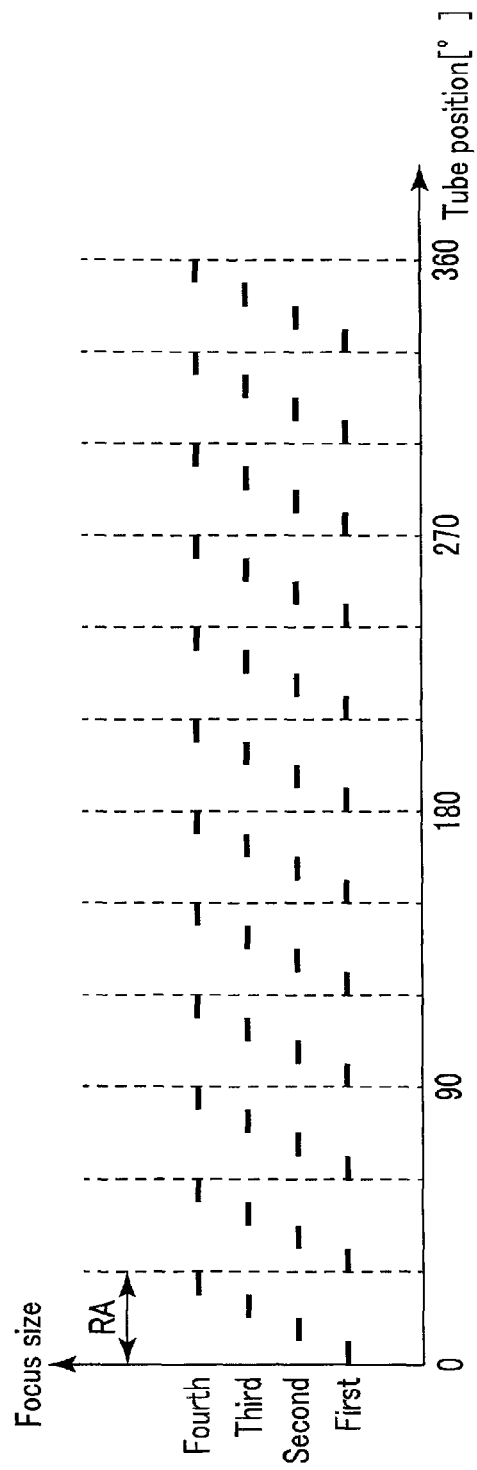
FIG. 4 illustrates a simplified CT imaging parameter acquisition sequence related to a correction data acquisition scan according to Example 1.

FIG. 4 illustrates a simplified CT imaging parameter acquisition sequence related to a correction data acquisition scan according to Example 1. The acquisition sequence represents the change in parameter values of the CT imaging parameter over the progress of the view period or in accordance with the change in the tube position. In FIG. 4, the ordinate represents parameter values of a CT imaging parameter, and the abscissa represents the rotation angle of the X-ray tube 13 about the rotation axis Z (a tube position) [°]. FIG. 4 is an example in which a target CT imaging parameter is the focus size. The focus size includes a first size, a second size, a third size, and a fourth size, which span the smallest size to the largest size. The unit-allowable angle range RA is set to be 30°, for example.

The gantry control circuitry 33 according to Example 1, in response to a correction data acquisition scan initiation instruction, synchronously controls the high-voltage X-ray device 17, the data acquisition circuitry 19, and the gantry motor 23, in accordance with the acquisition sequence information stored in the storage 107 to perform the correction data acquisition scan. Specifically, the gantry control circuitry 33 controls the gantry motor 23 to rotate the rotation frame 11 around the rotation axis Z. If the rotation speed of the rotation frame 11 reaches a predetermined speed, and the tube position of the X-ray tube 13 reaches a correction data acquisition scan initiation position, the gantry control circuitry 33 controls the high-voltage X-ray device 17 to allow the X-ray tube 13 to emit X-rays. The data acquisition circuitry 19 acquires, for each view, correction data through the X-ray detector 15. The correction data acquired for each view is stored in the storage 107. The correction data is associated with a view number, a type of CT imaging parameter, and a setting value.

While emitting X-rays, the gantry control circuitry 33 controls at least one of the high-voltage X-ray device 17 or the data acquisition circuitry 19 to sequentially alter the parameter values of the CT imaging parameter between the setting values within each unit-allowable angle range RA. For example, in FIG. 4, the gantry control circuitry 33 controls the high-voltage X-ray device 17 to sequentially alter the focus size from the first size, to the second size, to the third size, and to the fourth size within each unit-allowable angle range RA. The focus size is maintained for a predetermined angle interval (hereinafter referred to as a "stable period"). The stable period is determined by the imaging planning function 117 of the processing circuitry 101 based on the unit-allowable angle range RA, and the number of levels of the setting values to be altered in each unit-allowable angle range RA. For example, the processing circuitry 101 determines the stable period with a value obtained by dividing the unit-allowable angle range RA by the number of levels of the setting values. In FIG. 4, the unit-allowable angle range RA is 30°, and the number of levels of the setting values is four.

Accordingly, the stable period is determined as smaller than 30/4 [°]. In Example 1, the order of altering the focus size consists of an ascending order in each unit-allowable angle range RA over a single rotation.

The gantry control circuitry 33 acquires the correction data by controlling the data acquisition circuitry 19, while sequentially altering the focus size from the first size, to the second size, to the third size, and to the fourth size in each unit-allowable angle range RA during a single rotation of the rotation frame 11. Through this processing, the correction data for the first size, the second size, the third size, and the fourth size can be acquired during a single rotation of the rotation frame 11.

In FIG. 4, it is assumed that the CT imaging parameter is the focus size. However, the CT imaging parameter may be the focus position, a tube voltage, a tube current, a DAS gain, or the slit opening width. If the CT imaging parameter is the focus position, a tube voltage, a tube current, or the slit opening width, the gantry control circuitry 33 controls the gantry motor 23 to alter the parameter values of the corresponding CT imaging parameter. If the CT imaging parameter is a DAS gain, the gantry control circuitry 33 controls the data acquisition circuitry 19 to alter the parameter values of the CT imaging parameter.

The value of the CT imaging parameter is unstable when altering the levels of the setting values of the CT imaging parameter from the former level to the target level (transition period). Accordingly, the gantry control circuitry 33 may stop emission of X-rays from the X-ray tube 13 by controlling the high-voltage X-ray device 17 in the transition period. In addition, the gantry control circuitry 33 may stop acquisition of the correction data by controlling the data acquisition circuitry 19 in the transition period. Alternatively, the storage 107 may discard the correction data acquired by the data acquisition circuitry 19 in the transition period.

As shown in FIG. 4, the parameter value of the CT imaging parameter increases from the lower limit value to the upper limit value in each unit-allowable angle range RA. However, the change in the parameter value is not limited thereto.

Figure 5:
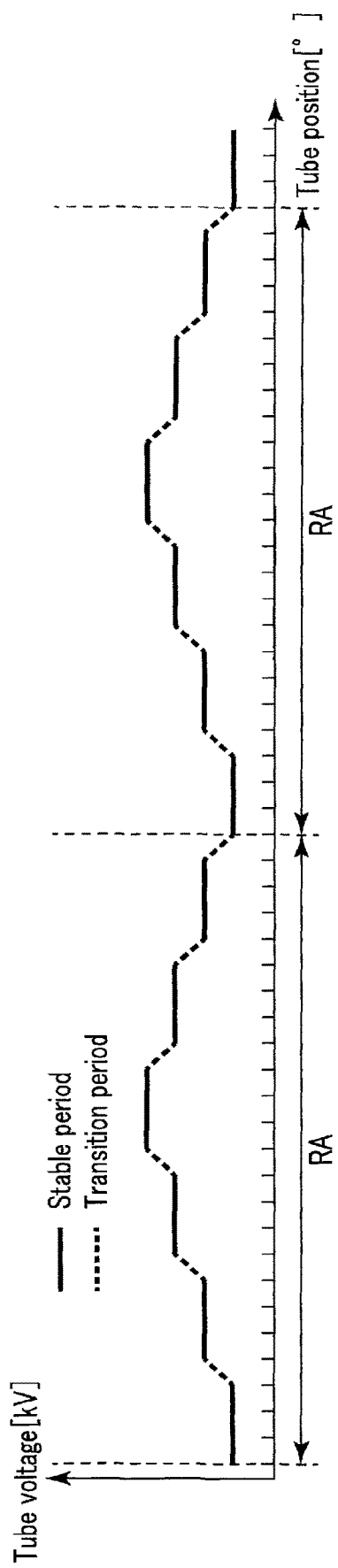
FIG. 5 illustrates another CT imaging parameter acquisition sequence related to a correction data acquisition scan according to Example 1.
Figure 6:
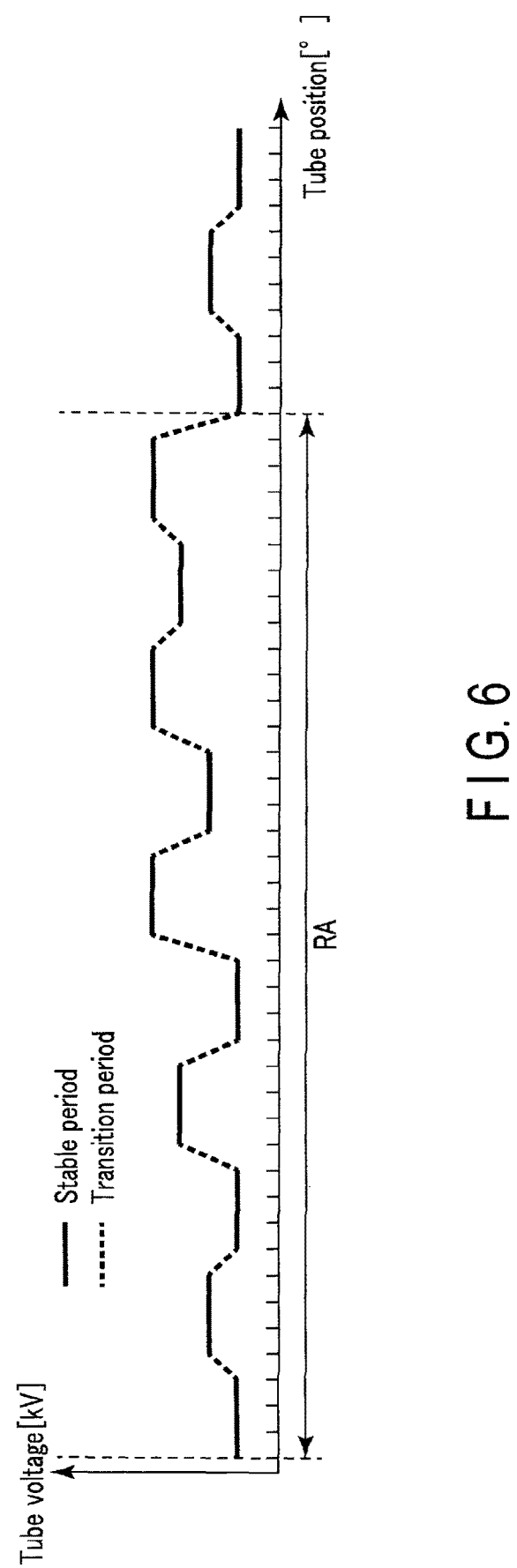
FIG. 6 illustrates another CT imaging parameter acquisition sequence related to a correction data acquisition scan according to Example 1.
Figure 7:
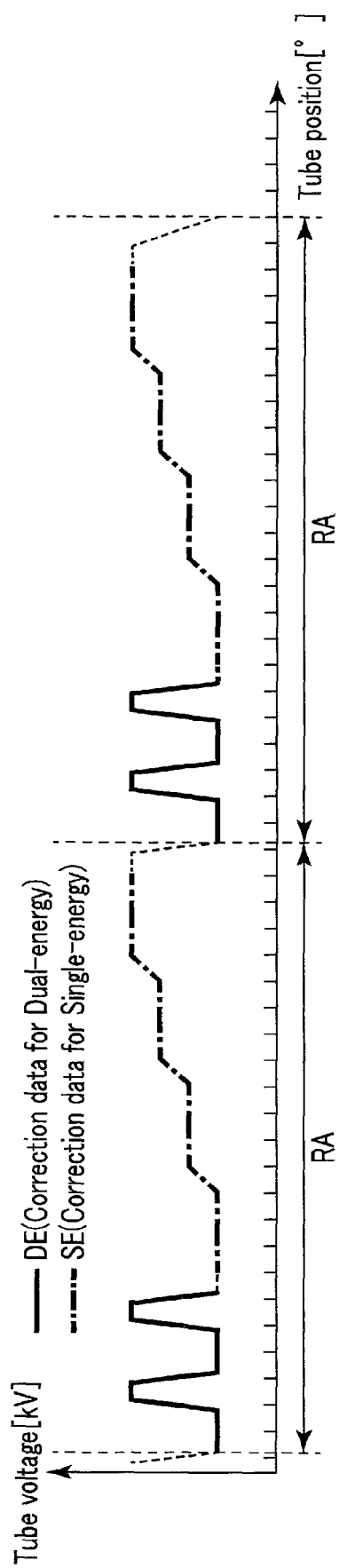
FIG. 7 illustrates another CT imaging parameter acquisition sequence related to a correction data acquisition scan according to Example 1.

FIGS. 5, 6 and 7 illustrate the other acquisition sequences of the CT imaging parameter for the correction data acquisition scan according to Example 1. FIGS. 5, 6 and 7 also illustrate the transition period. The CT imaging parameter is assumed to be a tube voltage [kV] in FIGS. 5, 6 and 7. The setting values of tube voltage include a first tube voltage value which is the lower limit value, a second tube voltage value, a third tube voltage value, and a fourth tube voltage value which is the upper limit value.

In the example of FIG. 5, the high-voltage X-ray device 17 discretely increases the tube voltage from the lower limit value to the upper limit value, and thereafter discretely decreases the tube voltage from the upper limit value to the lower limit value, in each unit-allowable angle range RA. In each unit-allowable angle range RA, the increase from the lower limit value to the upper limit value and the decrease from the upper limit value to the lower limit value are alternately repeated. The high-voltage X-ray device 17 maintains the tube voltage to be a constant value over three views (stable period), and alters the tube voltage values during a view (transition period) in each unit-allowable angle range RA.

In the example of FIG. 6, the high-voltage X-ray device 17 alternately switches the tube voltage between the lower limit value and the other setting values chosen from the lowest to the highest, and thereafter, alternately switches the tube voltage between the upper limit value and the other setting values chosen from the highest to the lowest in each unit-allowable angle range RA. The above alternating zig-zag pattern change is repeated in each unit-allowable angle range RA. The high-voltage X-ray device 17 maintains the tube voltage as a constant value over three views (stable period), and alters the tube voltage values during a view (transition period) in each unit-allowable angle range RA.

In the example of FIG. 7, the correction data for the tube voltages applied for the dual-energy (DE) mode, and the correction data for the tube voltages applied for the single-energy (SE) mode are sequentially acquired in each unit-allowable angle range RA. In this case, the high-voltage X-ray device 17 sequentially switches the tube voltage between the tube voltage values for the DE mode and the tube voltage values for the SE mode in each unit-allowable angle range RA. The tube voltage values for the DE mode may be two values, for example, a low voltage value (first tube voltage value) and a high voltage value (fourth tube voltage value). The tube voltage values for the SE mode may be four values, for example, a first tube voltage value, a second tube voltage value, a third tube voltage value, and a fourth tube voltage value. The high-voltage X-ray device 17 alternately switches the tube voltage between the low voltage value (first tube voltage value) and the high voltage value (fourth tube voltage value) to acquire the correction data for the DE mode, and thereafter, sequentially alters the tube voltage from the first tube voltage value, to the second tube voltage value, to the third tube voltage value, and to the fourth tube voltage value to acquire the correction data for the SE mode, in each unit-allowable angle range RA. The high-voltage X-ray device 17 maintains the tube voltage to be a constant value over three views (stable period), and alters the tube voltage values during a view (transition period) in each unit-allowable angle range RA.

As described above, the gantry control circuitry 33 according to Example 1 allows the X-ray tube 13 to emit X-rays, and discretely alters the setting values of a type of the CT imaging parameter with respect to which the correction data is acquired for each unit-allowable angle range, during a rotation of the rotation frame 11. The gantry control circuitry 33 according to Example 1 can acquire the correction data for the entire plurality of setting values of a type of the CT imaging parameter during a single rotation of the rotation frame 11, thereby, enabling swift acquisition of the correction data.

EXAMPLE 2

In Example 1, it is assumed that the CT imaging parameter value is discretely altered. However, the present embodiment is not limited thereto. In Example 2, the gantry control circuitry 33 consecutively changes the setting value of a type of CT imaging parameter with respect to which the correction data is acquired.

FIG. 8 illustrates a CT imaging parameter acquisition sequence for a correction data acquisition scan according to Example 2. FIG. 8 illustrates an example in which a target CT imaging parameter is the focus size, similar to FIG. 4. In FIG. 8, the ordinate represents a focus size, and the abscissa represents a tube position [°] in each graph. In Example 2, the setting values of the focus size are consecutive values from the lower limit value to the upper limit value.

As shown in FIG. 8, the gantry control circuitry 33 according to Example 2 controls the high-voltage X-ray device 17 to consecutively change the focus size within the range between the lower limit value and the upper limit value in each unit-allowable angle range RA. Specifically, various aspects can be applied for the consecutive change. For example, as shown in the graph at the top of FIG. 8, the high-voltage X-ray device 17 linearly alters the focus size from the lower limit value to the upper limit value in each unit-allowable angle range RA. In this case, the change in the focus size exhibits a triangle waveform. As shown in the graph in the middle of FIG. 8, the high-voltage X-ray device 17 linearly alters the focus size from the lower limit value to the upper limit value, and thereafter linearly changes the focus size from the upper limit value to the lower limit value, in each unit-allowable angle range RA. In this case, the change in the focus size exhibits a sawtooth waveform. Alternately repeating the increase and the decrease of the focus size can suppress an abrupt change in the focus size. As shown in the graph in the bottom of FIG. 8, the high-voltage X-ray device 17 non-linearly changes the focus size from the lower limit value to the upper limit value, and thereafter non-linearly changes the focus size from the upper limit value to the lower limit value, in each unit-allowable angle range RA. Specifically, the focus size is altered so that the rate of change over time is smaller in the vicinity of the upper limit value and the lower limit value, and the rate of change over time is greater in the middle of the upper and lower limit values. In this case, the change in the focus size exhibits a sine waveform. Setting the rate of change over time to be small in the vicinity of the upper and lower limit values can suppress an abrupt change in the focus size when switching the increase and the decrease of the focus size value.

The manner of change in the setting values of a CT imaging parameter such as the focus size, etc. may be designated by a user through the input circuitry 105. Via the imaging planning function 117, the processing circuitry 101 constructs the acquisition sequence so that the setting values of the CT imaging parameter are changed in each unit-allowable angle range in accordance with the designated manner of change.

As described above, the gantry control circuitry 33 according to Example 2 allows the X-ray tube 13 to generate X-rays and consecutively changes the setting value of a type of CT imaging parameter with respect to which the correction data is to be acquired in each unit-allowable angle range during a single rotation of the rotation frame 11. The gantry control circuitry 33 according to Example 2 can acquire the correction data for the entire plurality of setting values of a type of the CT imaging parameter during a single rotation of the rotation frame 11, thereby, enabling swift acquisition of the correction data.

EXAMPLE 3

In Examples 1 and 2, it is assumed that a type of the CT imaging parameter is targeted. However, the present embodiment is not limited thereto. In Example 3, two types of the CT imaging parameters are assumed to be targeted.

Figure 9:
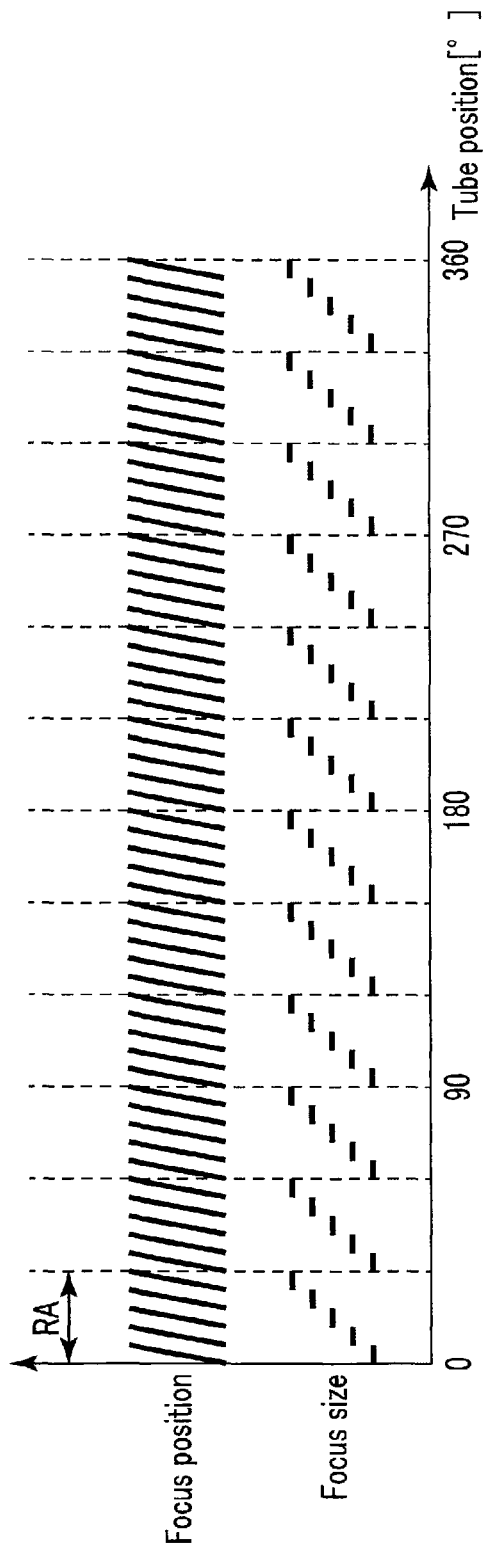
FIG. 9 illustrates a CT imaging parameter acquisition sequence related to a correction data acquisition scan according to Example 3.

FIG. 9 illustrates a CT imaging parameter acquisition sequence related for a correction data acquisition scan according to Example 3. FIG. 9 is an example in which the focus position and the focus size are targeted as CT imaging parameters for which the correction data is to be acquired. In FIG. 9, the ordinate represents a focus size and a focus position, and the abscissa represents a tube position [°]. In Example 3, the setting values of the focus position are consecutively changed from the lower limit value to the upper limit value, and the setting values of the focus size are altered stepwise from the lower limit value to the upper limit value.

First, the determination of the acquisition conditions for a correction data acquisition scan for two types of CT imaging parameters will be explained. By the imaging planning function 117, the processing circuitry 101 first selects two types of CT imaging parameters automatically or manually in response to a user's instruction through the input circuitry 105, and determines the setting values for the selected two types of CT imaging parameters by using the parameter table. For example, in the example of FIG. 9, the focus size and the focus position are selected as target CT imaging parameters. The setting values of the focus size are discrete values such as a first size, a second size, a third size, and a fourth size. The setting values of the focus position are consecutive values from the lower limit value to the upper limit value.

Next, the processing circuitry 101 sets one of the selected two types of CT imaging parameters as a CT imaging parameter for which the setting values are altered at a low speed (hereinafter referred to as a "low-speed switching parameter"), and sets the other parameter as a CT imaging parameter for which the setting values are altered at a higher speed than the low-speed switching parameter (hereinafter referred to as a "high-speed switching parameter"). For example, the processing circuitry 101 sets, among the selected two types of CT imaging parameters, a CT imaging parameter for which the setting values are discrete values for a low-speed switching parameter, and sets a CT imaging parameter for which the setting values are consecutive values for a high-speed switching parameter. If the selected two types of CT imaging parameters both have discrete setting values, the processing circuitry 101 compares the maximum capable switching speed between the two types of CT imaging parameters, sets a CT imaging parameter with a higher capable switching speed as a high-speed switching parameter, and sets a CT imaging parameter having a lower capable switching speed as a low-speed switching parameter. For example, in the example of FIG. 9, the setting values of the focus size are discrete values, and the setting values of the focus position are consecutive values. Accordingly, the focus size is set as a low-speed switching parameter, and the focus position is set as a high-speed switching parameter.

Thereafter, the processing circuitry 101 constructs an acquisition sequence so that the setting values of the low-speed switching parameter are discretely altered in a predetermined manner, and the setting values of the high-speed switching parameter are consecutively changed in a predetermined manner in each unit-allowable angle range RA. The temporal length of a stable period for each setting value of the low-speed switching parameter is set to be longer than the time required for alteration of all setting values of the high-speed switching parameter. For example, in the example of FIG. 9, the acquisition sequence is constructed so that the focus size is sequentially altered from the first size to the fourth size at regular intervals, and the focus position is linearly altered from the lower limit value to the upper limit value in a period in which each focus size is maintained in each unit-allowable angle range RA. The unit-allowable angle range RA is assumed to possess the range of angle required for altering all the setting values of the low-speed switching parameter. The acquisition sequence information is stored in the storage 107.

The gantry control circuitry 33 according to Example 3, in response to a correction data acquisition scan initiation instruction, synchronously controls the high-voltage X-ray device 17, the data acquisition circuitry 19, and the gantry motor 23, in accordance with the acquisition sequence information stored in the storage 107, in order to perform the correction data acquisition scan. Specifically, the gantry control circuitry 33 controls the gantry motor 23 to rotate the rotation frame 11 around the rotation axis Z. If the rotation speed of the rotation frame 11 reaches a predetermined speed, and the tube position of the X-ray tube 13 reaches a correction data acquisition scan initiation position, the gantry control circuitry 33 controls the high-voltage X-ray device 17 to allow the X-ray tube 13 to emit X-rays. The data acquisition circuitry 19 acquires, for each view, correction data through the X-ray detector 15. The correction data acquired for each view is stored in the storage 107. The correction data is associated with a view number, a type of CT imaging parameter, and a setting value.

While emitting X-rays, the gantry control circuitry 33 controls at least one of the high-voltage X-ray device 17 or the data acquisition circuitry 19 to sequentially alter the parameter value of the low-speed switching parameter between the plurality of setting values, and sequentially alter the parameter value of the high-speed switching parameter between the plurality of setting values during a period in which each of the setting values of the low-speed switching parameter is maintained, in each unit-allowable angle range RA. For example, in the example of FIG. 9, the gantry control circuitry 33 discretely alters the focus size from the lower limit value to the upper limit value, and consecutively alters the focus position from the lower limit value to the upper limit value for a period in which each of the setting values of the focus size is maintained, in each unit-allowable angle range RA. The gantry control circuitry 33 controls the data acquisition circuitry 19 to acquire the correction data while altering the low-speed switching parameter and the high-speed switching parameter to every setting values in each unit-allowable angle range RA, during a single rotation of the rotation frame 11. Through this processing, the correction data for all combinations of the setting values of the low-speed switching parameter and the setting values of the high-speed switching parameter can be swiftly acquired during a single rotation of the rotation frame 11.

Figure 10:
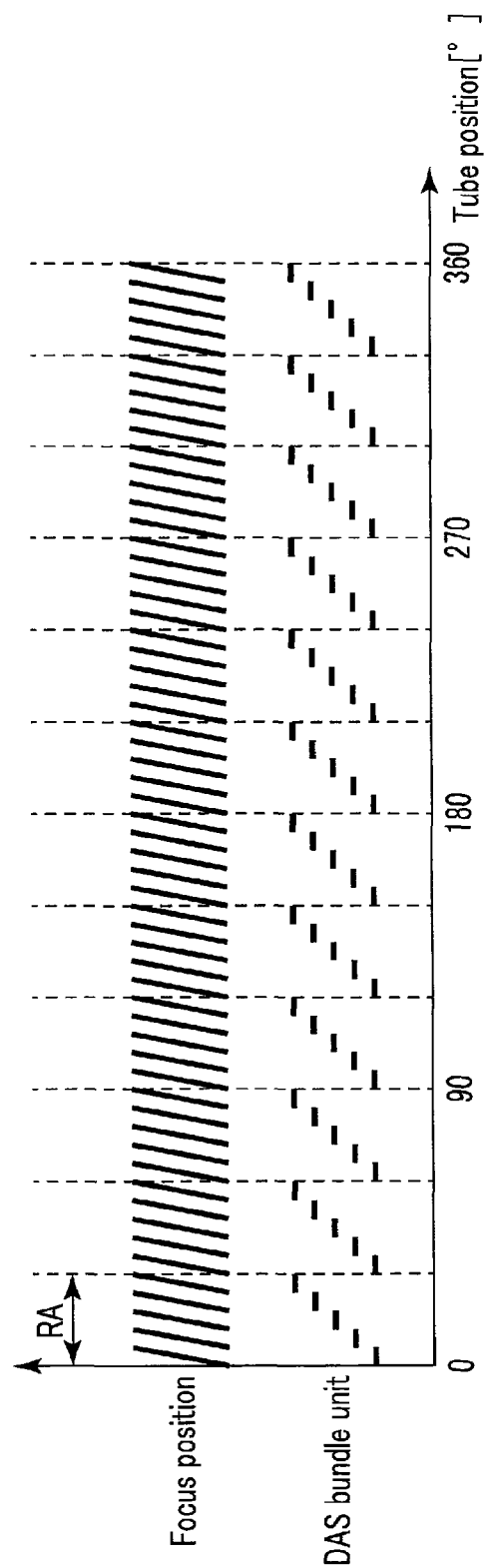
FIG. 10 illustrates another CT imaging parameter acquisition sequence related to a correction data acquisition scan according to Example 3.

The two types of CT imaging parameters are not limited to those explained above. For example, as shown in FIG. 10, the focus position and the DAS bundle units are set as target CT imaging parameters. In FIG. 10, the ordinate represents a focus position and DAS bundle units, and the abscissa represents a tube position [°]. In Example 3, the setting values of the focus position are consecutively altered from the lower limit value to the upper limit value. The setting values of the DAS bundle units are altered stepwise from the lower limit value (0.5 mm in FIG. 3) to the upper limit value (8.0 mm in FIG. 3). In this case, the focus position and the DAS bundle units are sequentially altered in a nesting manner during a single rotation of the rotation frame 11, as in the aforementioned processing. Through this processing, the correction data for the focus position and the DAS bundle units can be swiftly acquired.

EXAMPLE 4

In Examples 1, 2 and 3, all correction data can be acquired during a single rotation. However, there may be a case where all correction data cannot be acquired during a single rotation because the CT imaging parameter cannot be altered to all setting values within a unit-allowable angle range, for example. The X-ray computed tomography apparatus according to Example 4 determines the number of rotations.

By the imaging planning function 117, the processing circuitry 101 determines the number of rotations of the rotation frame 11 in a correction data acquisition scan, based on the ratio between the unit-allowable angle range and the minimum angle range required to alter the CT imaging parameter to all the setting values (hereinafter referred to as a "minimum angle range"). If the minimum angle range is equal to or less than the unit-allowable angle range, the processing circuitry 101 determines the number of rotations to be one. If the minimum angle range is greater than the unit-allowable angle range, and is equal to or less than a twofold of the unit-allowable angle range, the processing circuitry 101 determines the number of rotations to be two. Similarly, if the minimum angle range is greater than the twofold of the unit-allowable angle range, and is equal to or less than a threefold of the unit-allowable angle range, the processing circuitry 101 determines the number of rotation to be three. The minimum angle range may be determined, for example, based on the number of levels (the number of setting values) of a CT imaging parameter with respect to which the correction data is to be acquired, and the switching speed of the parameter value.

Figure 11:
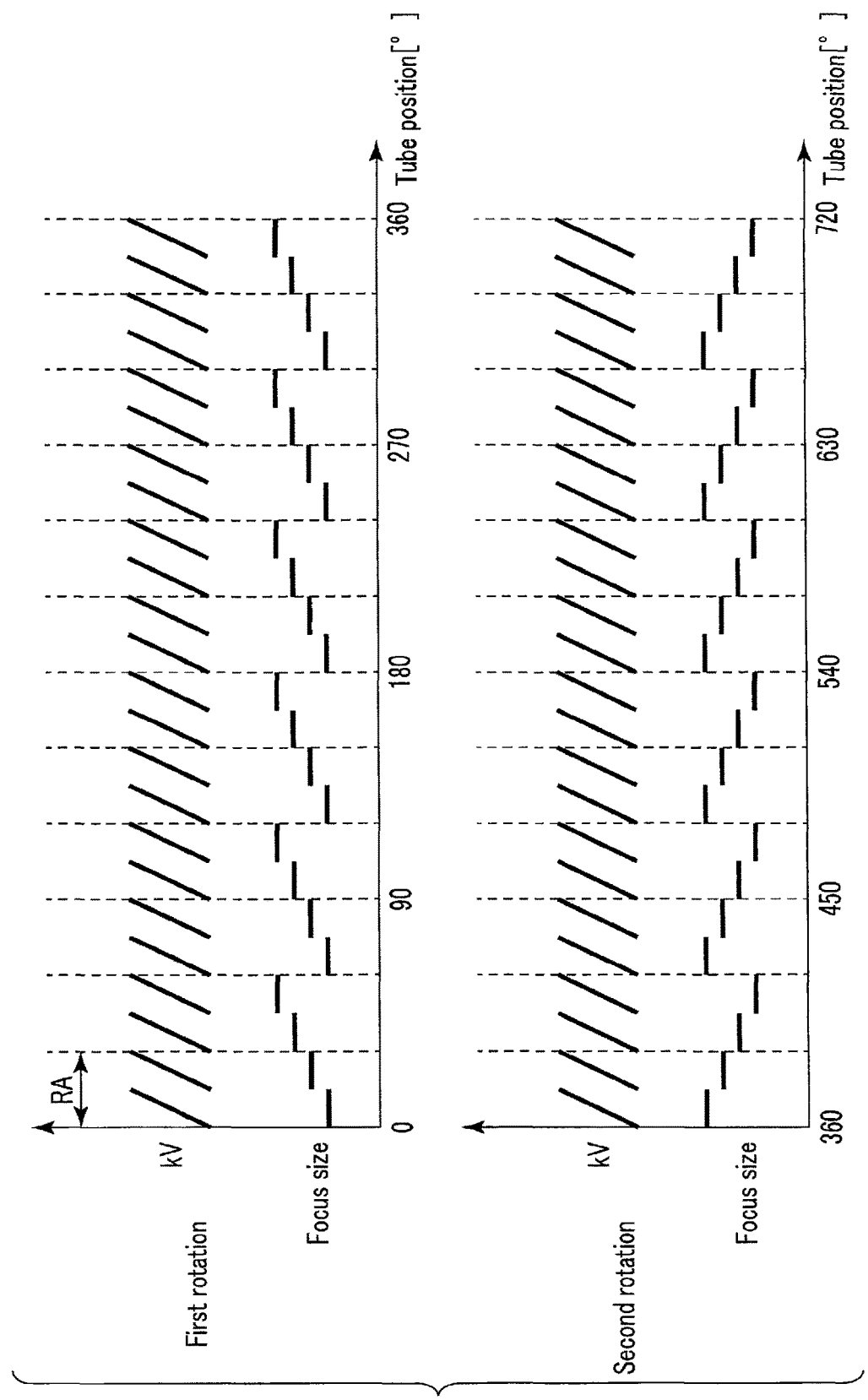
FIG. 11 illustrates a CT imaging parameter acquisition sequence related to a correction data acquisition scan according to Example 4.

FIG. 11 illustrates an acquisition sequence in which the number of rotations is set to be two. In FIG. 11, the tube position in the first rotation is changed from 0° to 360°, and the tube position in the second rotation is changed from 360° to 720°. It is assumed that the high-speed switching parameter is a tube voltage [kV], and the low-speed switching parameter is a focus size. As shown in FIG. 11, it is assumed that the changing speed of the tube voltage [kV] and the focus size is relatively low, and all the combinations of the setting values of the tube voltage [kV] and the focus size cannot be applied in a unit-allowable angle range RA. In this case, in accordance with the above method of determining the number of rotations, the number of rotations is determined as two.

In the case where the number of rotations is two, the gantry control circuitry 33 reverses the order of altering the low-speed switching parameter in the first and second rotations. Through this processing, the correction data for all the combinations of the setting values of the low-speed switching parameter and the setting values of the high-speed switching parameter can be acquired in each angle range. For example, as shown in FIG. 11, the focus size is altered from the first size to the fourth size in the ascending order during the first rotation, and is altered from the fourth size to the first size in the descending order during the second rotation. Accordingly, in a first unit-allowable angle range RA from 0° to 30° of the first rotation, the correction data for the first size and the second size is acquired, and in the same unit-allowable angle range RA (from 360° to 390°) of the second rotation, the correction data for the third size and fourth size is acquired. Through this processing, the correction data for all the combinations of the setting values of the focus size and the setting values of the tube voltage can be acquired in the angle range.

The order of altering the setting values should not be limited to the reversal in the first and second rotations for the low-speed switching parameter. Namely, the order of altering the setting values may be reversed for both the low-speed switching parameter and the high-speed switching parameter. In addition, even in the case of one type of the CT imaging parameter is targeted, the order of altering the setting values may be reversed in the first and second rotations.

EXAMPLE 5

The X-ray computed tomography apparatus 1 according to Example 5 acquires the correction data and measures afterglow of the X-ray detector 15.

FIG. 12 illustrates a correction data acquisition sequence according to Example 5. In the example of FIG. 12, a tube current NW is a target CT imaging parameter. As shown in FIG. 12, the gantry control circuitry 33 discretely alters the parameter value of the tube current from the lower limit value to the upper limit value in each unit-allowable angle range RA. The gantry control circuitry 33 controls the high-voltage X-ray device 17 to repeatedly emit pulse X-rays in synchronism with the timing of changing the parameter value of the tube current. The peak value of an electric signal output by the X-ray detector 15 during an X-ray emission pause period RO exhibits a non-linear shape depending on the tube voltage or the tube current. The gantry control circuitry 33 controls the data acquisition circuitry 19 to acquire the correction data through the X-ray detector 15 not only in the period when the pulse X-rays are emitted (i.e., the stable period of the tube current), but also in the X-ray emission pause period RO. The correction data acquired in the X-ray emission pause period RO is greatly affected by afterglow of the X-ray detector 15. The correction data acquired in the X-ray emission pause period RO is referred to as afterglow data. The afterglow data is stored in the storage 107. The afterglow data is associated with a tube position, a type of CT imaging parameter, and a preceding setting value.

In Example 5, the gantry control circuitry 33 stops X-ray emission when altering levels of the CT imaging parameter, and acquires afterglow data in the X-ray emission pause period. Through this processing, the efficiency of afterglow data acquisition can be improved.

In the above example, the afterglow data is assumed to be acquired when altering levels of the CT imaging parameter. However, the present embodiment is not limited thereto. The afterglow data may be acquired at any time during an X-ray emission pause period.

Figure 13:
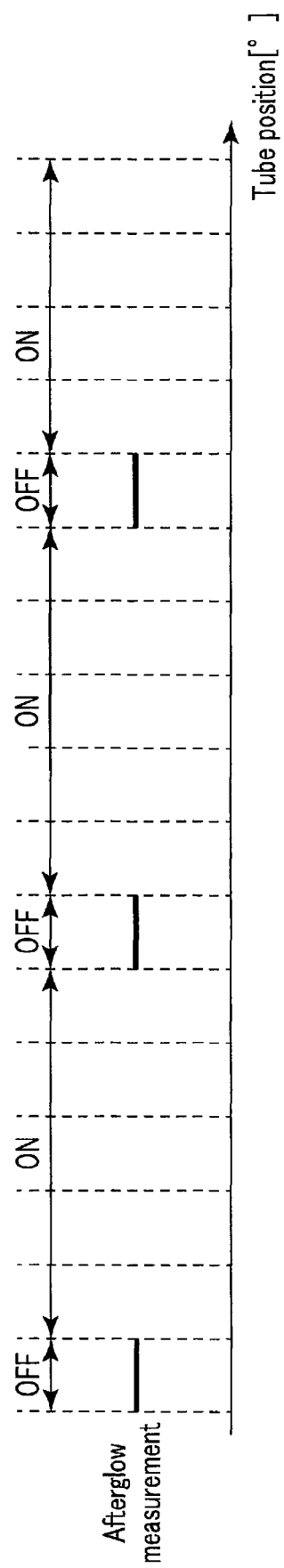
FIG. 13 illustrates anther acquisition sequence according to Example 5.

FIG. 13 illustrates anther acquisition sequence according to Example 5. As shown in FIG. 13, the gantry control circuitry 33 controls the high-voltage X-ray device 17 to repeat emission and stop emission of X-rays. The gantry control circuitry 33 controls the high-voltage X-ray device 17 to emit X-rays in an X-ray emission period ON. The X-ray emission period ON and the X-ray emission pause period OFF may be set in any tube position range. In the X-ray emission period ON, the gantry control circuitry 33 may emit X-rays without changing the parameter value of the CT imaging parameter, or may control at least one of the high-voltage X-ray device 17 or the data acquisition circuitry 19 to alter the parameter value of the CT imaging parameter for acquisition of the correction data. In the X-ray emission pause period OFF, the gantry control circuitry 33 controls the data acquisition circuitry 19 to acquire afterglow data.

Since the image quality is not important for the afterglow data, the X-ray emission pause period can be provided more often or for a long period in comparison with a scan targeted for imaging, as described above. Accordingly, the gantry control circuitry 33 of Example 5 can acquire afterglow data efficiently.

As described in Examples 1 to 5, the X-ray computed tomography apparatus 1 according to the present embodiment includes the X-ray tube 13, the X-ray detector 15, the rotation frame 11, the gantry control circuitry 33, and the data acquisition circuitry 19. The X-ray tube 13 generates X-rays. The X-ray detector 15 detects X-rays generated by the X-ray tube 13. The rotation frame 11 supports the X-ray tube 13 and the X-ray detector 15 rotatably around the rotation axis Z. While the X-ray tube 13 and the X-ray detector 15 are rotated, the gantry control circuitry 33 allows the X-ray tube 13 to generate X-rays and alters a predetermined CT imaging parameter within a predetermined parameter value range, for which correction data is acquired, in each unit-allowable angle range which permits the change in the output or the sensitivity of the X-ray detector 15. While the X-ray tube 13 and the X-ray detector 15 are rotated, the data acquisition circuitry 19 acquires the correction data for the predetermined parameter value range of the predetermined CT imaging parameter through the X-ray detector 15.

With the above configuration, the X-ray computed tomography apparatus 1 according to the present embodiment alters a CT imaging parameter within a predetermined parameter value range in each unit-allowable angle range determined based on the dependency of the output or the sensitivity of the X-ray detector relative to the tube position. Since the purpose of the correction data acquisition scan is acquisition of correction data, the image quality is not important, in contrast to the normal scan which images a subject. Namely, since in the correction data acquisition scan, the parameter values of the CT imaging parameter can be altered in terms of the levels, manners of change, and degrees of change that are not allowed for the normal scan which need to ensure the image quality, the acquisition sequence that focuses on the efficiency of correction data acquisition can be constructed. Accordingly, even in the case where the number of setting values of each CT imaging parameter is large, the correction data for all the setting values can be acquired in a smaller number of rotations in comparison with the conventional technique.

According to at least one or more embodiments, the correction data can be acquired in high efficiency.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. An X-ray computed tomography apparatus comprising:
an X-ray tube that generates X-rays;
an X-ray detector that detects X-rays generated by the X-ray tube;
a gantry that supports the X-ray tube and the X-ray detector rotatably about a rotation axis;
control circuitry that allows the X-ray tube to generate X-rays and alters a predetermined CT imaging parameter for which correction data is acquired during a single rotation of the X-ray tube and the X-ray detector, while the X-ray tube and the X-ray detector are rotated; and
acquisition circuitry that acquires correction data for the predetermined CT imaging parameter through the X-ray detector, while the X-ray tube and the X-ray detector are rotated,
wherein the control circuitry sequentially alters a first parameter to multiple levels in each unit angle range, and sequentially alters a second parameter to multiple levels within each of the multiple levels of the first parameter, the first parameter and the second parameter corresponding to the predetermined CT imaging parameter.

2. The X-ray computed tomography apparatus according to claim 1, wherein
the control circuitry alters the predetermined CT imaging parameter within a predetermined parameter value range in each unit angle range that accepts a change in output or sensitivity of the X-ray detector relative to a rotation angle about the rotation axis.

3. The X-ray computed tomography apparatus according to claim 2, further comprising processing circuitry that determines the unit angle range in accordance with at least one of a type of the predetermined CT imaging parameter, a slice thickness, and a rotation speed about the rotation axis.

4. The X-ray computed tomography apparatus according to claim 1, further comprising processing circuitry that determines a number of rotations of the X-ray tube and the X-ray detector, based on a ratio between the unit angle range and an angle range required to alter the first parameter to all setting values.

5. The X-ray computed tomography apparatus according to claim 1, wherein
the control circuitry rotates the X-ray tube and the X-ray detector one time for acquisition of the correction data, if the unit angle range is sufficient for altering the first parameter to all the setting values.

6. The X-ray computed tomography apparatus according to claim 1, wherein
the control circuitry rotates the X-ray tube and the X-ray detector for a number of times which has been determined based on a ratio between the unit angle range and an angle range required to alter the first parameter to all setting values, in order to acquire the correction data, if the unit angle range is not sufficient for altering the first parameter to all the setting values.

7. The X-ray computed tomography apparatus according to claim 6, wherein
the control circuitry reverses an order of altering parameter values of the first parameter in a first rotation and a second rotation of the X-ray tube and the X-ray detector.

8. The X-ray computed tomography apparatus according to claim 1, wherein
the control circuitry stops emission of X-rays from the X-ray tube when altering levels of the first parameter, if the first parameter is altered in multiple levels,
the acquisition circuitry acquires the correction data for measuring afterglow of the X-ray detector during a period in which emission of X-rays from the X-ray tube is stopped.

9. The X-ray computed tomography apparatus according to claim 1, further comprising processing circuitry that sets at least two types of parameters selected from an X-ray focus size, an X-ray focus position, a tube voltage, a tube current, a DAS gain, a slit opening width, and DAS bundle units, as CT imaging parameters, each of which corresponds to the CT imaging parameter.

* * * * *